US010092321B2

(12) United States Patent
Fischvogt et al.

(10) Patent No.: US 10,092,321 B2
(45) Date of Patent: Oct. 9, 2018

(54) BLADELESS OBTURATORS AND BLADELESS OBTURATOR MEMBERS

(71) Applicant: Covidien LP, Mansfield, MA (US)

(72) Inventors: Gregory Fischvogt, Hamden, CT (US); Robert C. Smith, Middlefield, CT (US)

(73) Assignee: Covidien LP, Mansfield, MA (US)

(*) Notice: Subject to any disclaimer, the term of this patent is extended or adjusted under 35 U.S.C. 154(b) by 397 days.

(21) Appl. No.: 14/628,580

(22) Filed: Feb. 23, 2015

(65) Prior Publication Data
US 2015/0164551 A1 Jun. 18, 2015

Related U.S. Application Data

(63) Continuation of application No. 13/212,232, filed on Aug. 18, 2011, now Pat. No. 8,961,552.
(Continued)

(51) Int. Cl.
A61B 17/34 (2006.01)
A61B 17/00 (2006.01)
A61B 17/32 (2006.01)

(52) U.S. Cl.
CPC ...... *A61B 17/3496* (2013.01); *A61B 17/3421* (2013.01); *A61B 2017/00907* (2013.01);
(Continued)

(58) Field of Classification Search
CPC ............ A61B 17/3421; A61B 17/3496; A61B 2017/00907; A61B 2017/320044; A61B 2017/3454
See application file for complete search history.

(56) References Cited

U.S. PATENT DOCUMENTS 4,535,773 A 8/1985 Yoon
4,601,710 A 7/1986 Moll
(Continued)

FOREIGN PATENT DOCUMENTS

EP E0604197 6/1994
EP 1712196 A2 10/2006
(Continued)

OTHER PUBLICATIONS

Canadian Office Action dated Jul. 27, 2017 issued in Canadian Application No. 2,750,378.
(Continued)

*Primary Examiner* — Julie A Szpira

(57) ABSTRACT

A surgical obturator that includes an elongated shaft defining a longitudinal axis and an obturator member disposed adjacent a distal end of the elongated shaft. The obturator member may include a proximal section being convex along a majority of its length. It may also include a central section disposed adjacent the proximal section, the central section including a first pair of surfaces disposed relative to each other on radially opposite sides of the central section, and a second set of surfaces disposed between the first pair of surfaces and further being disposed relative to each other on radially opposite sides of the central section, at least a portion of a length of each one of the first pair of surfaces being concave, and at least a portion of a length of each one of the second pair of surfaces being convex. The obturator member may also include a guiding nub disposed distally of the central section and including a rounded distal-most portion. The rounded distal-most portion of the guiding nub may be atraumatic to tissue.

17 Claims, 10 Drawing Sheets

Related U.S. Application Data

(60) Provisional application No. 61/384,893, filed on Sep. 21, 2010.

(52) U.S. Cl.
CPC ............. *A61B 2017/320044* (2013.01); *A61B 2017/349* (2013.01); *A61B 2017/3454* (2013.01); *A61B 2017/3456* (2013.01)

(56) References Cited

U.S. PATENT DOCUMENTS

| | | | |
|---|---|---|---|
| 4,654,030 A | 3/1987 | Moll et al. | |
| 5,066,288 A | 11/1991 | Deniega et al. | |
| 5,104,382 A | 4/1992 | Brinkerhoff et al. | |
| 5,215,526 A | 6/1993 | Deniega et al. | |
| 5,224,952 A | 7/1993 | Deniega et al. | |
| 5,226,891 A | 7/1993 | Bushatz et al. | |
| 5,232,440 A | 8/1993 | Wilk | |
| 5,248,298 A | 9/1993 | Bedi et al. | |
| 5,314,417 A | 5/1994 | Stephens et al. | |
| 5,364,372 A | 11/1994 | Danks et al. | |
| 5,366,445 A | 11/1994 | Haber et al. | |
| 5,372,588 A | 12/1994 | Farley et al. | |
| 5,387,197 A | 2/1995 | Smith et al. | |
| 5,399,167 A | 3/1995 | Deniega | |
| 5,411,515 A | 5/1995 | Haber et al. | |
| 5,471,705 A | 12/1995 | Dao | |
| 5,478,317 A | 12/1995 | Yoon | |
| 5,487,745 A | 1/1996 | McKenzie | |
| 5,522,833 A | 6/1996 | Stephens et al. | |
| 5,533,977 A | 7/1996 | Metcalf et al. | |
| 5,538,509 A | 7/1996 | Dunlap et al. | |
| 5,545,150 A | 8/1996 | Danks et al. | |
| 5,554,137 A | 9/1996 | Young et al. | |
| 5,554,167 A | 9/1996 | Young et al. | |
| 5,569,160 A | 10/1996 | Sauer et al. | |
| 5,591,192 A * | 1/1997 | Privitera | A61B 1/00087 600/114 |
| 5,607,440 A | 3/1997 | Danks et al. | |
| 5,609,604 A | 3/1997 | Schwemberger et al. | |
| 5,624,459 A | 4/1997 | Kortenbach et al. | |
| 5,658,236 A | 8/1997 | Sauer et al. | |
| 5,669,885 A | 9/1997 | Smith | |
| 5,676,156 A | 10/1997 | Yoon | |
| 5,690,663 A | 11/1997 | Stephens | |
| 5,690,664 A | 11/1997 | Sauer et al. | |
| 5,697,913 A | 12/1997 | Sierocuk et al. | |
| 5,709,671 A | 1/1998 | Stephens et al. | |
| 5,772,660 A | 6/1998 | Young et al. | |
| 5,776,112 A | 7/1998 | Stephens et al. | |
| 5,797,943 A | 8/1998 | Danks et al. | |
| 5,824,002 A | 10/1998 | Gentelia et al. | |
| 5,827,315 A | 10/1998 | Yoon | |
| 5,843,115 A | 12/1998 | Morejon | |
| 5,860,996 A | 1/1999 | Urban et al. | |
| 5,868,773 A | 2/1999 | Danks et al. | |
| 5,879,332 A | 3/1999 | Schwemberger et al. | |
| 5,893,369 A | 4/1999 | LeMole | |
| 5,904,699 A | 5/1999 | Schwemberger et al. | |
| 5,913,848 A | 6/1999 | Luther et al. | |
| 5,916,232 A | 6/1999 | Hart | |
| 5,947,930 A | 9/1999 | Schwemberger et al. | |
| 5,980,493 A | 11/1999 | Smith et al. | |
| 5,984,941 A * | 11/1999 | Wilson | A61B 17/3496 604/256 |
| 5,997,510 A | 12/1999 | Schwemberger | |
| 6,017,356 A | 1/2000 | Frederick et al. | |
| 6,022,367 A | 2/2000 | Sherts | |
| 6,030,402 A | 2/2000 | Thompson et al. | |
| 6,036,657 A | 3/2000 | Milliman et al. | |
| 6,063,099 A | 5/2000 | Danks et al. | |
| 6,228,058 B1 | 5/2001 | Dennis et al. | |
| 6,319,226 B1 | 11/2001 | Sherry | |
| 6,497,687 B1 | 12/2002 | Blanco | |
| 6,497,716 B1 | 12/2002 | Green et al. | |
| 6,544,277 B1 | 4/2003 | O'Heeron et al. | |
| 6,613,063 B1 | 9/2003 | Hunsberger | |
| 6,656,198 B2 | 12/2003 | Tsonton et al. | |
| 6,685,630 B2 | 2/2004 | Sauer et al. | |
| 6,716,201 B2 * | 4/2004 | Blanco | A61B 17/3494 604/164.01 |
| 6,719,746 B2 | 4/2004 | Blanco | |
| 6,830,578 B2 * | 12/2004 | O'Heeron | A61B 17/3417 604/170.01 |
| 6,835,201 B2 | 12/2004 | O'Heeron et al. | |
| 6,837,874 B1 | 1/2005 | Popov | |
| 6,884,253 B1 * | 4/2005 | McFarlane | A61B 17/3417 604/164.01 |
| 6,960,164 B2 | 11/2005 | O'Heeron | |
| D518,177 S | 3/2006 | Blanco | |
| D531,726 S | 11/2006 | Blanco et al. | |
| 7,320,694 B2 * | 1/2008 | O'Heeron | A61B 17/3417 606/167 |
| 7,344,519 B2 | 3/2008 | Wing et al. | |
| 7,758,603 B2 | 7/2010 | Taylor et al. | |
| 8,961,552 B2 | 2/2015 | Fischvogt et al. | |
| 2002/0004646 A1 | 1/2002 | Manhes | |
| 2003/0100914 A1 | 5/2003 | O'Heeron et al. | |
| 2003/0109894 A1 | 6/2003 | Blanco | |
| 2004/0230155 A1 * | 11/2004 | Blanco | A61B 17/3494 604/26 |
| 2004/0230217 A1 | 11/2004 | O'Heeron | |
| 2005/0033304 A1 | 2/2005 | O'Heeron | |
| 2005/0038466 A1 | 2/2005 | O'Heeron et al. | |
| 2005/0065543 A1 | 3/2005 | Kahle et al. | |
| 2005/0075655 A1 * | 4/2005 | Bumbalough | A61B 17/11 606/153 |
| 2005/0107816 A1 * | 5/2005 | Pingleton | A61B 17/3417 606/185 |
| 2005/0119676 A1 | 6/2005 | Bumbalough et al. | |
| 2005/0203559 A1 | 9/2005 | O'Heeron | |
| 2005/0209623 A1 | 9/2005 | Patton | |
| 2005/0261717 A1 | 11/2005 | Sauer et al. | |
| 2006/0030870 A1 | 2/2006 | Staudner | |
| 2006/0149302 A1 | 7/2006 | Popov | |
| 2006/0173479 A1 * | 8/2006 | Smith | A61B 1/00135 606/185 |
| 2006/0200095 A1 | 9/2006 | Steube | |
| 2006/0200182 A1 | 9/2006 | Prosek | |
| 2006/0226655 A1 | 10/2006 | Smith | |
| 2007/0005087 A1 | 1/2007 | Smith et al. | |
| 2007/0010842 A1 | 1/2007 | Popov | |
| 2007/0016237 A1 | 1/2007 | Smith | |
| 2008/0300617 A1 | 12/2008 | Smith | |
| 2009/0093833 A1 * | 4/2009 | Smith | A61B 17/3417 606/185 |
| 2009/0306697 A1 | 12/2009 | Fischvogt | |
| 2010/0318112 A1 * | 12/2010 | Smith | A61B 17/34 606/185 |

FOREIGN PATENT DOCUMENTS

| | | |
|---|---|---|
| EP | 1997447 A1 | 12/2008 |
| EP | 2044899 A2 | 4/2009 |
| WO | 9404082 A1 | 3/1994 |
| WO | 0201998 | 1/2002 |
| WO | 03026512 A1 | 4/2003 |
| WO | 03096879 A2 | 11/2003 |

OTHER PUBLICATIONS

Extended European Search Report dated Feb. 3, 2012 issued by the European Patent Office in corresponding European Patent Application No. 11 250 784.3.
Australian Examination Report dated Sep. 23, 2014 issued in Australian Application No. 2011218604.
Australian Examination Report dated Jun. 11, 2014 issued in Australian Application No. 2011218604.
Japanese Office Action dated Mar. 13, 2015 issued in Japanese Application No. 2011-196351.

(56) References Cited

OTHER PUBLICATIONS

Japanese Office Action dated Jul. 2, 2015, issued in JP Application No. 2011-196351.

* cited by examiner

BLADELESS OBTURATORS AND BLADELESS OBTURATOR MEMBERS

CROSS REFERENCE TO RELATED APPLICATION

The present application is a continuation of U.S. patent application Ser. No. 13/212,232, filed Aug. 18, 2011, which claims the benefit of and priority to U.S. Provisional Application Ser. No. 61/384,893 filed on Sep. 21, 2010. The entire contents of each of these applications is incorporated by reference herein.

BACKGROUND

Technical Field

The present disclosure relates generally to bladeless obturators and bladeless obturator members for guiding through tissue in an endoscopic procedure and, more specifically, for the blunt dissection of the abdominal lining during a surgical procedure.

SUMMARY OF THE INVENTION

The present invention, in accordance with various example embodiments thereof, relates to a surgical obturator that includes an elongated shaft defining a longitudinal axis and an obturator member disposed adjacent a distal end of the elongated shaft. The obturator member may include a proximal section being convex along a majority of its length; a central section disposed adjacent the proximal section and including a first pair of surfaces disposed relative to each other on radially opposite sides of the central section, and a second set of surfaces disposed between the first pair of surfaces and further being disposed relative to each other on radially opposite sides of the central section, at least a portion of a length of each one of the first pair of surfaces being concave, and at least a portion of a length of each one of the second pair of surfaces being convex; and a guiding nub disposed distally of the central section and including a rounded distal-most portion. The rounded distal-most portion of the guiding nub may be atraumatic to tissue. A majority of a length of the guiding nub may be cylindrical and/or a majority of a length of the guiding nub may be substantially parallel to the longitudinal axis. A transverse cross-section of a portion of the central section may be substantially oval, or, in other embodiments, may be a circle. In some embodiments, at least a portion of the proximal section may extend radially outwardly of an imaginary line disposed between a proximal-most surface of the proximal section and the distal-most portion of the guiding nub. At least a portion of the central section may extend radially outwardly of the imaginary line. Additionally or alternatively, at least a portion of the guiding nub may extend radially outwardly of the imaginary line. In various embodiments, the entire length of each one of the first pair of surfaces may be concave, and the entire length of each one of the second pair of surfaces may be convex. The proximal section may be convex along its entire length. Advantageously, at least a portion of the obturator member may be one of transparent and translucent.

In other embodiments, the present invention may relate to a surgical trocar assembly that includes a cannula and a surgical obturator, at least a portion of the surgical obturator being configured for insertion through the cannula. The surgical obturator may include an obturator housing, an elongated shaft extending distally from the obturator housing and defining a longitudinal axis, and an obturator member disposed adjacent a distal end of the elongated shaft. The obturator member may include a proximal section being convex along a majority of its length. The obturator member may also include a central section disposed adjacent the proximal section and including a first surface and a second surface. The second surface may be disposed about 90 degrees about the circumference of the central section relative to the first surface. A majority of a length of the first surface may be concave, and a majority of a length of the second surface may be convex. The obturator member may also include a guiding nub extending distally from the central section and may include a rounded distal-most portion.

BRIEF DESCRIPTION OF FIGURES

Various embodiments of the presently disclosed bladeless obturators and bladeless obturator members are disclosed herein with reference to the drawings, wherein.

DETAILED DESCRIPTION

Figure 1:
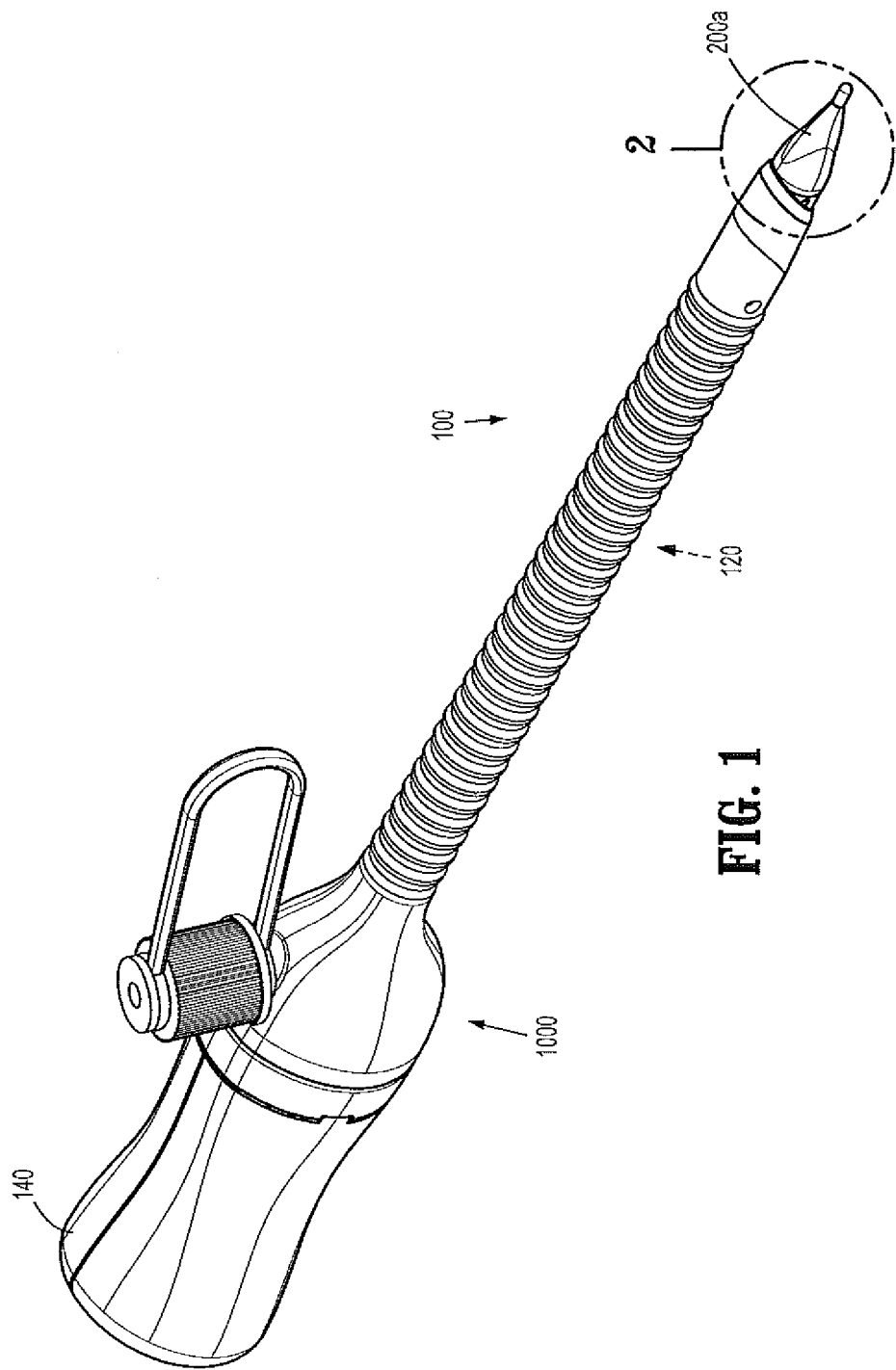
FIG. 1 is a perspective view of a bladeless obturator including a first embodiment of a bladeless obturator member at its distal end.
Figure 2:
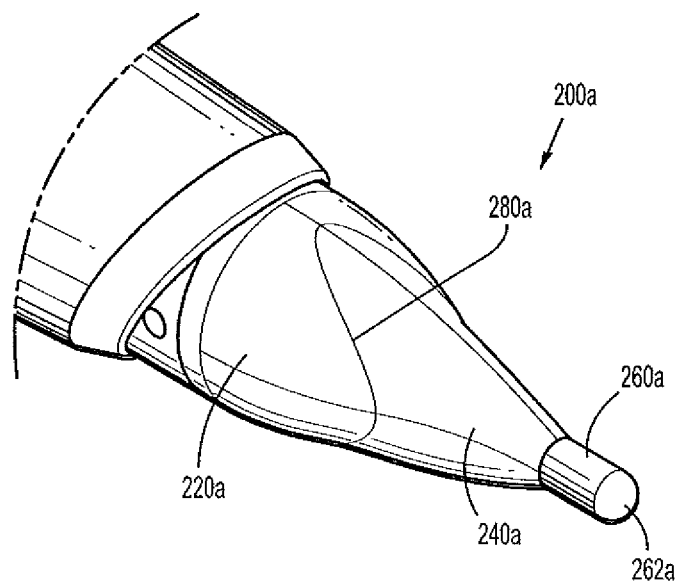
FIG. 2 is perspective view of the bladeless obturator member of FIG. 1.

Embodiments of the presently disclosed bladeless obturators and bladeless obturator members are described in detail with reference to the drawings, wherein like reference numerals designate corresponding elements in each of the several views.

The bladeless obturator 100 of each embodiment of the present disclosure includes an obturator shaft 120, an obturator housing 140 and a bladeless obturator member 200. The obturator shaft 120 extends distally from the obturator housing 140. The bladeless obturator member 200 is disposed adjacent the distal end of the obturator shaft 120. The bladeless obturator member 200 is insertable through a cannula assembly 1000 and into tissue. Three embodiments of the bladeless obturator member 200 are shown in the accompanying figures: FIGS. 1-6 illustrate a first embodiment of bladeless obturator member 200a; FIGS. 7-12 illustrate a second embodiment of bladeless obturator member 200b; and FIGS. 13-19 illustrate a third embodiment of bladeless obturator member 200c.

With reference to FIGS. 1-6, the first embodiment of bladeless obturator member 200a is shown. Bladeless obturator member 200a includes a proximal section 220a, a central section 240a, and a rounded guiding nub 260a. An imaginary line 280a (shown to illustrate curvature) shows proximal section 220a relative to central section 240a.

Figure 3:
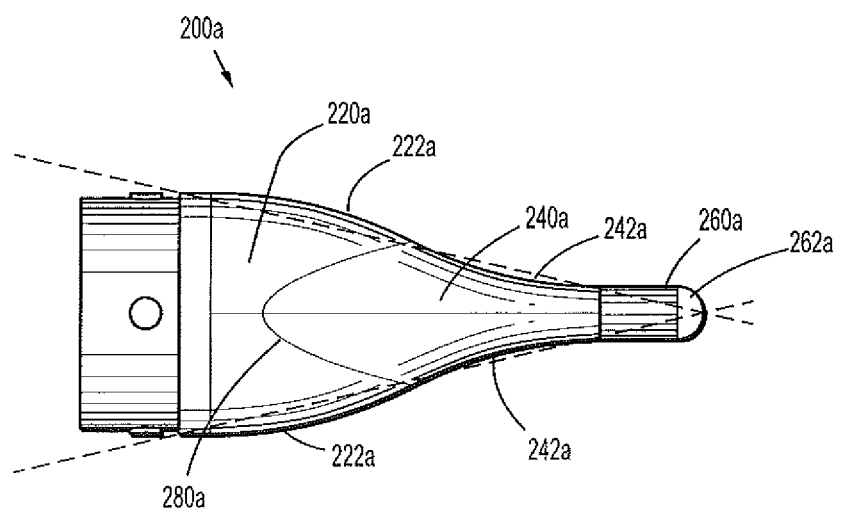
FIG. 3 is a top plan view of the bladeless obturator member of FIG. 1, the bottom plan view being a mirror image of the top plan view.

With particular reference to FIG. 3, a top view of bladeless obturator member 200a is shown. In this view, proximal section 220a includes a pair of convex surfaces 222a, and central section 240a includes a pair of concave surfaces 242a. Rounded guiding nub 260a extends distally from central section 240a and is generally cylindrical and includes a rounded, e.g., defined by a radius curve, distal-most portion 262a, which is atraumatic to tissue. Additionally, as shown in connection with the phantom lines in FIG. 3 that represent a cone, a portion of both the proximal section 220a and the rounded guiding nub 260a of bladeless obturator member 200a are outside of the dimensions of the cone.

Figure 4:
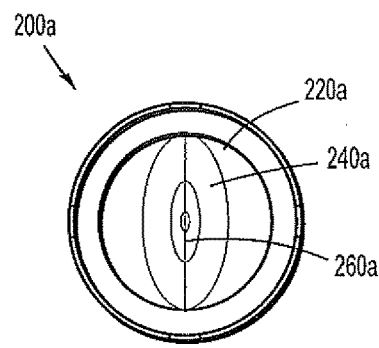
FIG. 4 is a proximal end view of the bladeless obturator member of FIG. 1 viewed from the proximal end of the bladeless obturator member looking toward the distal end of the bladeless obturator member.
Figure 5:
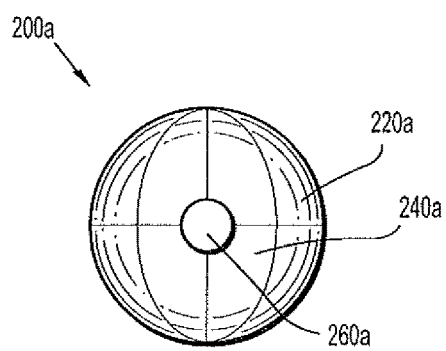
FIG. 5 is a distal end view of the bladeless obturator member of FIG. 1 viewed from the distal end of the bladeless obturator member looking toward the proximal end of the bladeless obturator member.

With reference to FIG. 5, which illustrates a distal-to-proximal view of the bladeless obturator member 200a, the end view of the rounded guiding nub 260a is circular, the end view of central section 240a is oval, and the end view of the proximal section 220a is circular. FIG. 4 illustrates a proximal-to-distal view of the bladeless obturator member 200a showing the hollow interior thereof.

Figure 6:
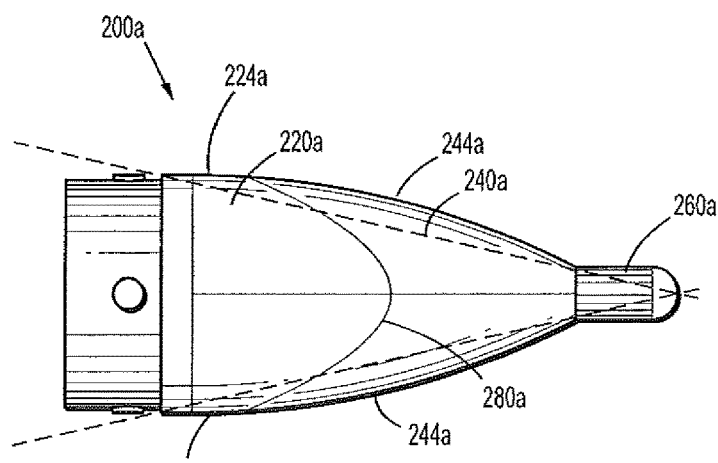
FIG. 6 is a right side elevation view of the bladeless obturator member of FIG. 1, the left side elevation view being a mirror image of the right side elevation view.
Figure 7:
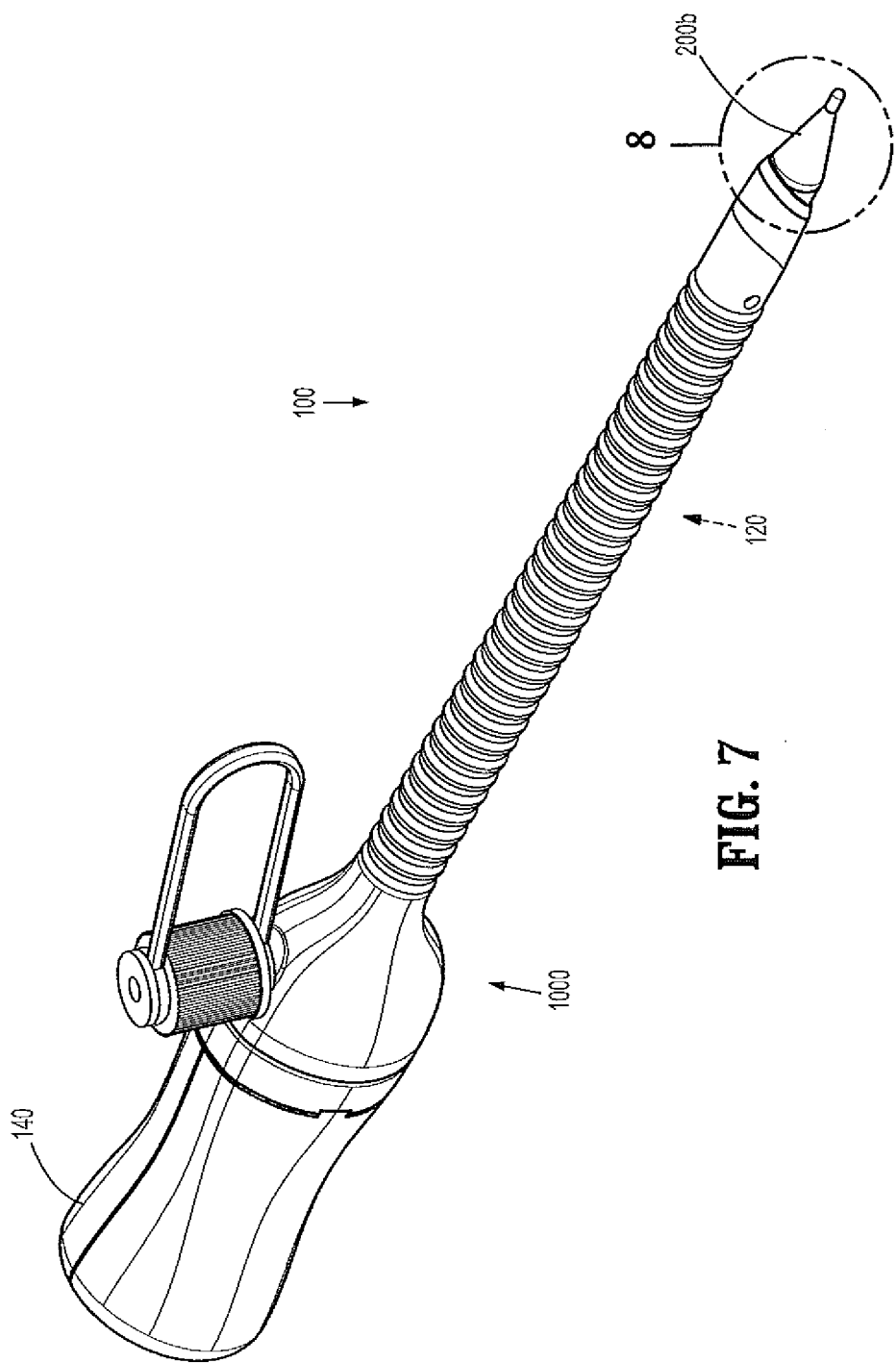
FIG. 7 is a perspective view of a bladeless obturator including a second embodiment of a bladeless obturator member at its distal end.
Figure 8:
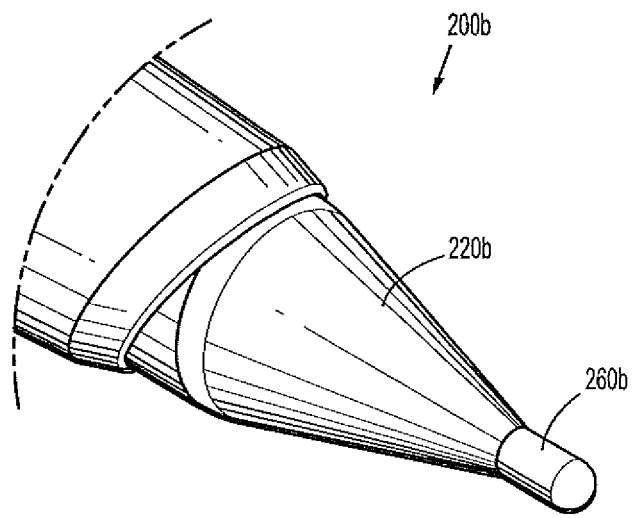
FIG. 8 is perspective view of the bladeless obturator member of FIG. 7.

With reference to FIG. 6, a side view of bladeless obturator member 200a is shown. This view of bladeless obturator member 200a is radially offset 90° from the top view of bladeless obturator member 200a of FIG. 3. In this view, outer surfaces 224a of proximal section 220a are generally linear and/or convex, and outer surfaces 244a of central section 240a are convex. That is, central section 240a includes both concave (FIG. 3) and convex (FIG. 6) portions. Additionally, as shown in connection with the phantom lines in FIG. 6 that represent a cone, a portion of the proximal section 220a, the central section 240a, and the rounded guiding nub 260a of bladeless obturator member 200a are outside of the dimensions of the cone.

Rounded guiding nub 260a permits initial insertion within an opening, e.g., a pre-cut scalpel incision, in the tissue and facilitates the advancement of the bladeless obturator member 200a between the tissue layers to gently dissect tissue, without any cutting or incising of the tissue. After initial insertion and continued distal insertion, central section 240a and proximal portion 220a continue to gently enlarge the opening in tissue.

In various embodiments at least a portion of the bladeless obturator member 200a is clear and/or translucent. In these embodiments, the clear/translucent bladeless obturator member 200a facilitates viewing tissue adjacent the bladeless obturator member 200a during the insertion and/or advancement of the bladeless obturator 100 and/or an instrument, for example.

With reference to FIGS. 7-12 the second embodiment of bladeless obturator member 200b is shown. Bladeless obturator member 200b includes a conical section 220b, and a rounded guiding nub 260b.

Figure 9:
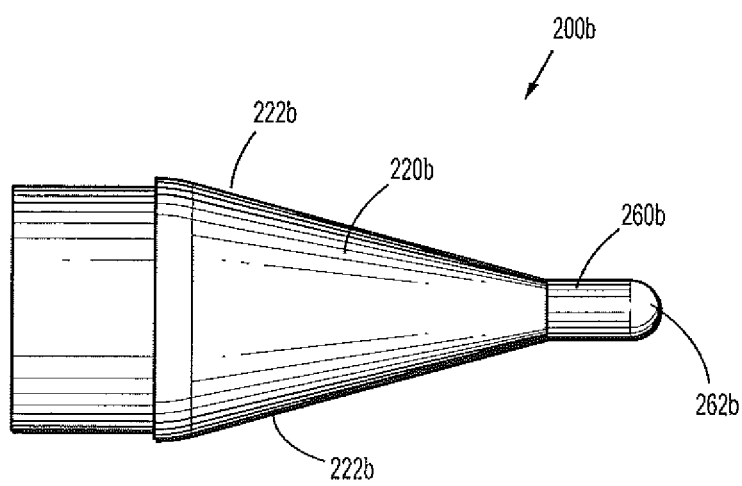
FIG. 9 is a top plan view of the bladeless obturator member of FIG. 7, the bottom plan view being a mirror image of the top plan view.

With particular reference to FIG. 9, a top view of bladeless obturator member 200b is shown. In this view, conical section 220b includes a pair of generally linear surfaces 222b. Rounded guiding nub 260b extends distally from conical section 220b and is generally cylindrical and includes a rounded, e.g., defined by a radius curve, distal-most portion 262b, which is atraumatic to tissue.

Figure 10:
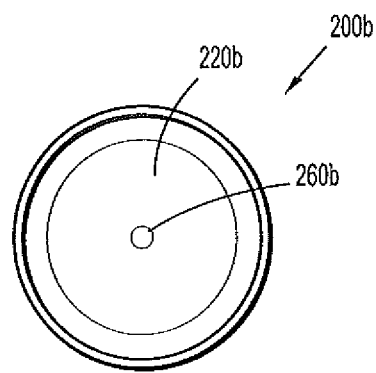
FIG. 10 is a proximal end view of the bladeless obturator member of FIG. 7 viewed from the proximal end of the bladeless obturator member looking toward the distal end of the bladeless obturator member.
Figure 11:
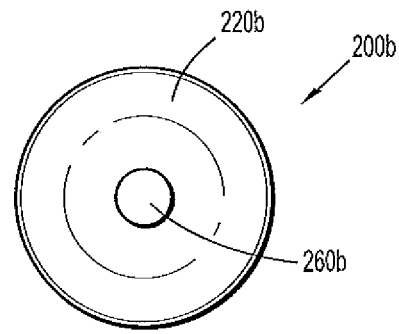
FIG. 11 is a distal end view of the bladeless obturator member of FIG. 7 viewed from the distal end of the bladeless obturator member looking toward the proximal end of the bladeless obturator member.

With reference to FIG. 11, which illustrates a distal-to-proximal view of the bladeless obturator member 200b, the end view of the rounded guiding nub 260b is circular, and the end view of the conical section 220b is circular. FIG. 10 illustrates a proximal-to-distal view of the bladeless obturator member 200b showing the hollow interior thereof.

Figure 12:
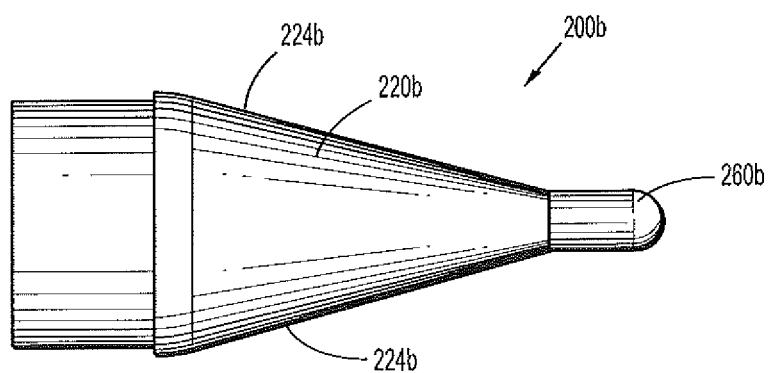
FIG. 12 is a right side elevation view of the bladeless obturator member of FIG. 7, the left side elevation view being a mirror image of the right side elevation view.
Figure 13:
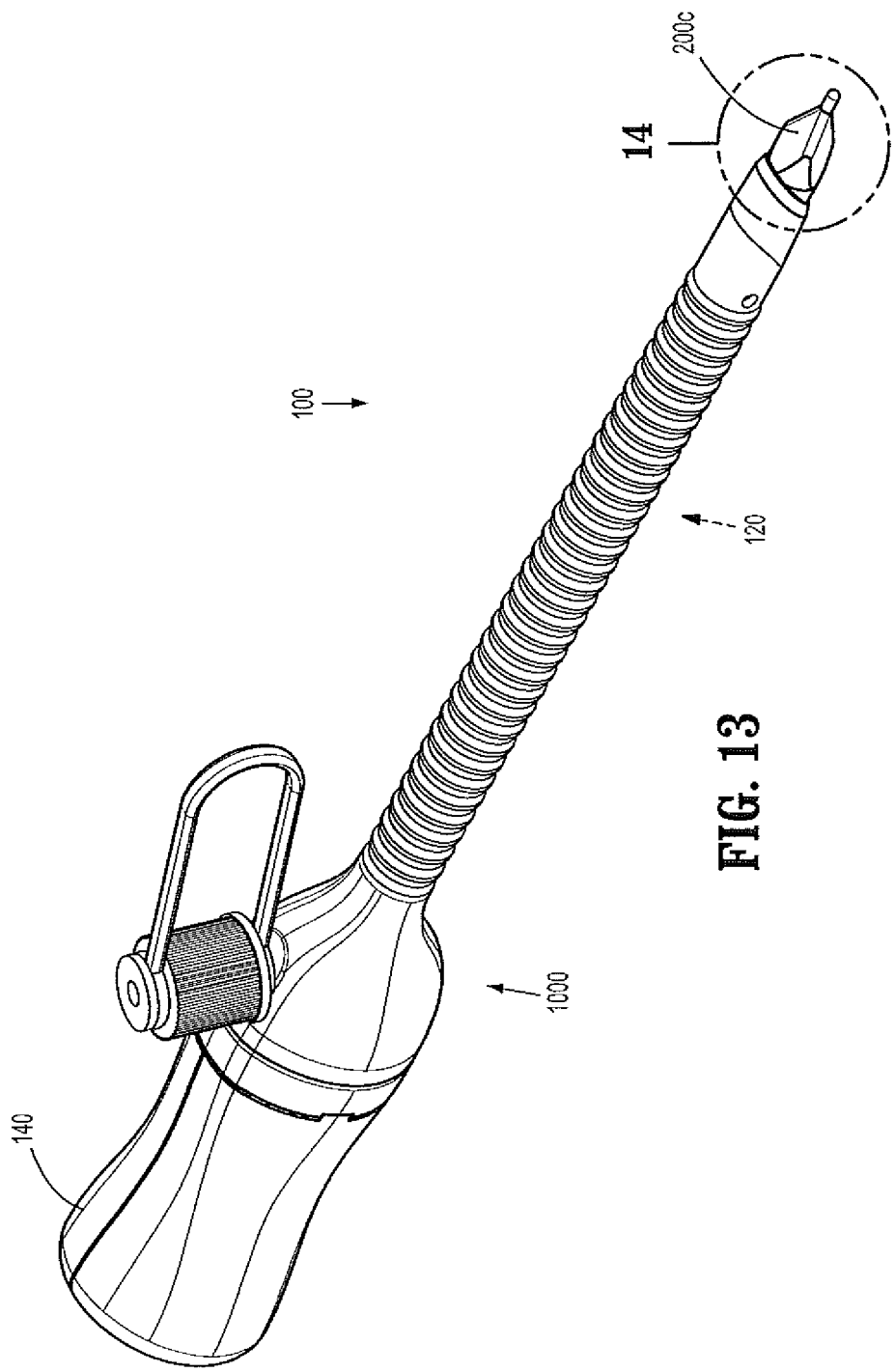
FIG. 13 is a perspective view of a bladeless obturator including a third embodiment of a bladeless obturator member at its distal end.
Figure 14:
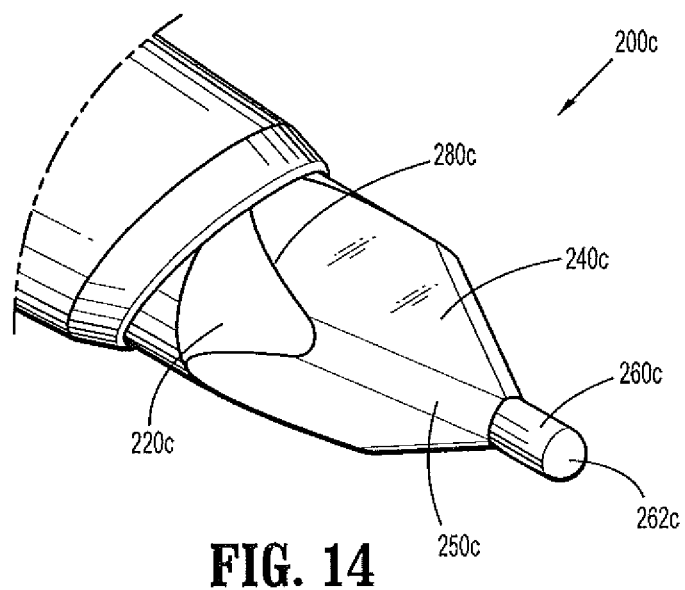
FIG. 14 is perspective view of the bladeless obturator member of FIG. 13.

With reference to FIG. 12, a side view of bladeless obturator member 200b is shown. This view of bladeless obturator member 200b is radially offset 90° from the top view of bladeless obturator member 200b of FIG. 9. In this view, outer surfaces 224b of conical section 220b are generally linear.

Rounded guiding nub 260b permits initial insertion within an opening, e.g., a pre-cut scalpel incision, in the tissue and facilitates the advancement of the bladeless obturator member 200b between the tissue layers to gently dissect tissue, without any cutting or incising of the tissue. After initial insertion and continued distal insertion, conical section 220b continues to gently enlarge the opening in tissue.

In various embodiments at least a portion of the bladeless obturator member 200b is clear and/or translucent. In these embodiments, the clear/translucent bladeless obturator member 200b facilitates viewing tissue adjacent the bladeless obturator member 200b during the insertion and/or advancement of the bladeless obturator 100 and/or an instrument, for example.

With reference to FIGS. 13-19, the third embodiment of bladeless obturator member 200c is shown. Bladeless obturator member 200c includes a proximal section 220c, a central section 240c, and a rounded guiding nub 260c. An undulating line 280c separates proximal section 220c from central section 240c.

Figure 15:
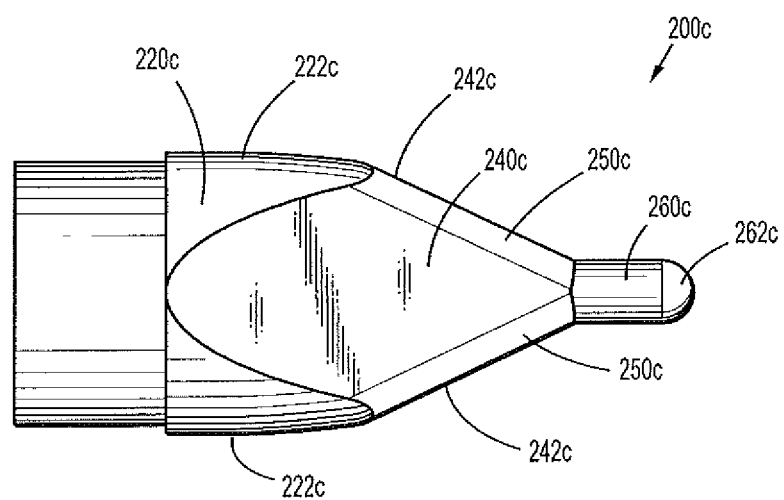
FIG. 15 is a top plan view of the bladeless obturator member of FIG. 13.

With particular reference to FIG. 15, a top view of bladeless obturator member 200c is shown. In this view, proximal section 220c includes a pair of generally linear/convex surfaces 222c, a majority of which are generally parallel with a longitudinal axis defined by obturator shaft 120. In this view, central section 240c includes a pair of generally linear surfaces 242c, which are tapered toward rounded guiding nub 260c. Rounded guiding nub 260c extends distally from central section 240c and is generally cylindrical and includes a rounded, e.g., defined by a radius curve, distal-most portion 262c, which is atraumatic to tissue.

Figure 16:
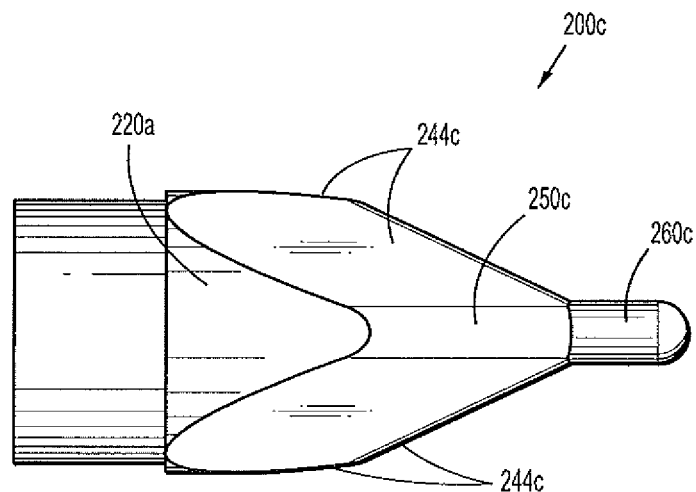
FIG. 16 is a bottom plan view of the bladeless obturator member of FIG. 13.

With reference to FIG. 16, a bottom view of bladeless obturator member 200c is shown. In this view, surfaces 244c of central section 240c include a proximal portion that is substantially parallel to the longitudinal axis, and distal portion that is tapered toward rounded guiding nub 260c.

Figure 17:
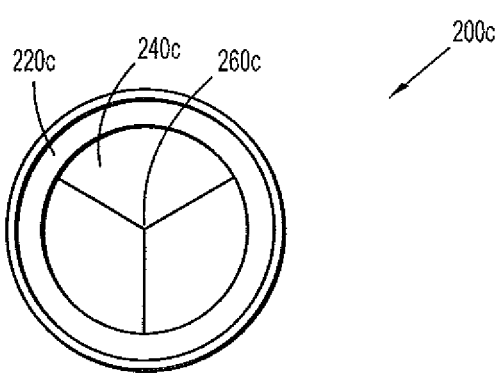
FIG. 17 is a proximal end view of the bladeless obturator member of FIG. 13 viewed from the proximal end of the bladeless obturator member looking toward the distal end of the bladeless obturator member.
Figure 18:
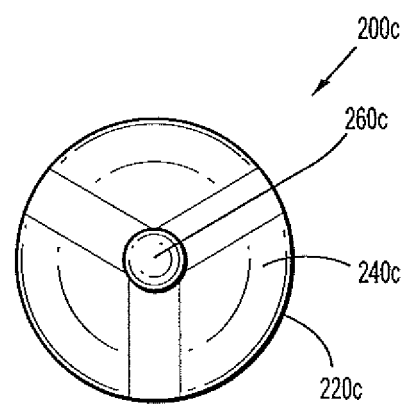
FIG. 18 is a distal end view of the bladeless obturator member of FIG. 13 viewed from the distal end of the bladeless obturator member looking toward the proximal end of the bladeless obturator member.

With reference to FIG. 18, which illustrates a distal-to-proximal view of the bladeless obturator member 200c, the end view of the rounded guiding nub 260c is circular, the end view of central section 240c is circular, and the end view of the proximal section 220a is circular. FIG. 17 illustrates a proximal-to-distal view of the bladeless obturator member 200c showing the hollow interior thereof.

Figure 19:
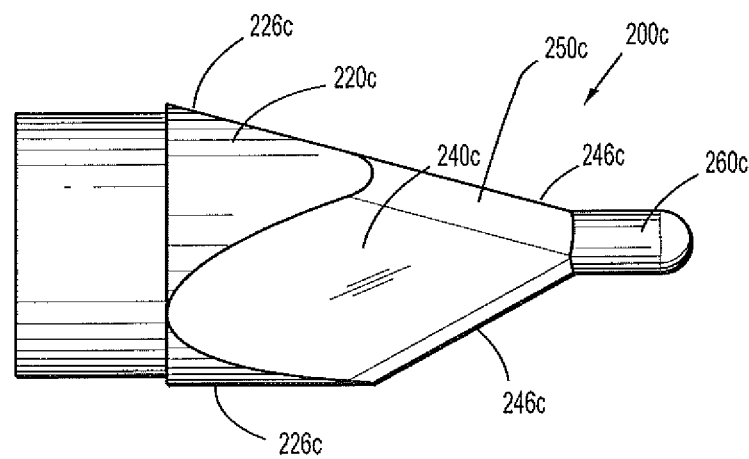
FIG. 19 is a right side elevation view of the bladeless obturator member of FIG. 13, the left side elevation view being a mirror image of the right side elevation view.

With reference to FIG. 19, a side view of bladeless obturator member 200c is shown. This view of bladeless obturator member 200c is radially offset 90° from the top view of bladeless obturator member 200c of FIG. 15. In this view, outer surfaces 226c of proximal section 220c are generally linear tapered toward rounded guiding nub 260c (upper surface), and generally linear and substantially parallel to the longitudinal axis (lower surface). Outer surfaces 246c of central section are generally linearly tapered toward rounded guiding nub 260c.

Thus, as can be appreciated with reference to FIGS. 13-19, central section 240c of bladeless obturator member 200c is generally pyramidal in shape (with three faces), and includes a flat portion 250c at the intersections between each of the three faces. Additionally, the proximal surface of central section 240c is undulated, as defined by undulating line 280c.

Rounded guiding nub 260c permits initial insertion within an opening, e.g., a pre-cut scalpel incision, in the tissue and facilitates the advancement of the bladeless obturator member 200c between the tissue layers to gently dissect tissue, without any cutting or incising of the tissue. After initial insertion and continued distal insertion, central section 240c and proximal portion 220c continue to gently enlarge the opening in tissue.

In various embodiments at least a portion of the bladeless obturator member 200c is clear and/or translucent. In these embodiments, the clear/translucent bladeless obturator member 200c facilitates viewing tissue adjacent the bladeless obturator member 200c during the insertion and/or advancement of the bladeless obturator 100 and/or an instrument, for example.

In use, the bladeless obturator 100 is introduced within cannula assembly 1000 and the assembled unit is positioned against the targeted tissue, e.g., the abdominal lining. The bladeless obturator member 200 is manipulated relative to the tissue whereby the rounded guiding nub 260 engages tissue and gently dissects or separates the tissue to gain access to an underlying cavity. The bladeless obturator 100 may then be removed from the cannula assembly 1000. Instruments may be introduced within the cannula assembly 1000 to perform a surgical procedure.

While various embodiments of the disclosure have been shown in the figures, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope and spirit of the present disclosure.

What is claimed is:

1. An obturator member comprising:
    a proximal section being convex along a majority of its length;
    a central section adjacent the proximal section and longitudinally contiguous therewith, the central section including a first pair of surfaces disposed on radially opposite sides of the central section and a second pair of surfaces with each surface of the second pair of surfaces positioned adjacent each surface of the first pair of surfaces, each surface of the first pair of surfaces being longitudinally concave and entirely convex in cross-section, and each of the second pair of surfaces being longitudinally convex; and
    a guiding nub longitudinally contiguous with the central section and extending longitudinally therefrom, the guiding nub including a rounded distal-most portion.

2. The obturator member according to claim 1, wherein the second pair of surfaces are disposed relative to each other on radially opposite sides of the central section.

3. The obturator member according to claim 1, wherein the central section has a contiguous outer surface.

4. The obturator member according to claim 1, wherein the obturator member is configured to minimize cutting or incising surrounding tissue structures such that the obturator member may be advanced into a body cavity in an exposed condition.

5. The obturator member according to claim 1, wherein the proximal section defines a pair of radially opposed and distally-extending regions, and wherein the first pair of surfaces of the central portion extend from the pair of radially opposed and distally-extending regions.

6. The obturator member according to claim 1, wherein the obturator member is configured to be disposed at a distal end of a shaft.

7. The obturator member according to claim 6, wherein the obturator member is configured to be coupled to the distal end of the shaft.

8. The obturator member according to claim 7, wherein the rounded distal-most portion of the guiding nub is configured to be atraumatic to tissue.

9. The obturator member according to claim 7, wherein the guiding nub is cylindrical along a majority of its length.

10. The obturator member according to claim 7, wherein a transverse cross-section of the central section is substantially oval in shape.

11. The obturator member according to claim 7, wherein a transverse cross-section of a proximal-most portion of the proximal section is circular in shape.

12. The obturator member according to claim 7, wherein the entire length of each surface of the first pair of surfaces is concave.

13. The obturator member according to claim 7, wherein the entire length of each surface of the second pair of surfaces is convex.

14. The obturator member according to claim 7, wherein a portion of the obturator member is transparent or translucent.

15. A surgical obturator comprising:
    an elongated shaft defining a longitudinal axis; and
    an obturator member positioned at a distal end of the elongated shaft and having a length along the longitudinal axis, the obturator member comprising:

a proximal section being convex along a majority of its length;

a central section longitudinally contiguous with and extending longitudinally from the proximal section, the central section including a first pair of surfaces disposed on radially opposite sides of the central section and a second pair of surfaces with each surface of the second pair of surfaces positioned adjacent each surface of the first pair of surfaces, each surface of the first pair of surfaces being longitudinally concave and entirely convex in cross-section, and each surface of the second pair of surfaces being longitudinally convex; and a guiding nub longitudinally contiguous with and extending longitudinally from the central section, the guiding nub including a rounded distal-most portion.

16. An obturator member comprising:

a proximal section being convex along a majority of its length;

a central section longitudinally contiguous with and extending longitudinally from the proximal section, the central section including a first surface and a second surface positioned radially adjacent the first surface, the first surface being longitudinally concave and entirely convex in cross-section, and the second surface being longitudinally convex; and a guiding nub longitudinally contiguous with and extending longitudinally from the central section, the guiding nub including a rounded distal-most portion.

17. The obturator member according to claim 16, wherein the guiding nub is longitudinally fixed relative to the central section.

* * * * *